United States Patent [19]

Williams

[11] 4,326,518
[45] Apr. 27, 1982

[54] SEPARABLE INTEGRAL DONOR CONNECTOR WITH MANUAL CLAMPING MEANS

[75] Inventor: Ronald A. Williams, Mundelein, Ill.
[73] Assignee: Baxter Travenol Laboratories, Inc., Deerfield, Ill.
[21] Appl. No.: 138,031
[22] Filed: Apr. 7, 1980
[51] Int. Cl.³ ............................................... A61M 5/00
[52] U.S. Cl. ....................................... 128/214.2; 251/7
[58] Field of Search ........... 128/214 R, 214 C, 214 D, 128/214.2, 247, 274; 251/7, 10

[56] References Cited

U.S. PATENT DOCUMENTS

| | | | |
|---|---|---|---|
| 1,190,039 | 7/1916 | Tatum | 251/10 |
| 2,961,664 | 11/1960 | Davidson | 251/7 |
| 3,127,892 | 4/1964 | Bellamy et al. | 128/214 R |
| 3,142,472 | 7/1964 | Lipschutz | 251/10 |
| 3,217,710 | 11/1965 | Beall et al. | 128/214 R |
| 3,342,179 | 9/1967 | Ellmann | 128/214.2 |
| 4,136,694 | 1/1979 | Kuehn | 128/214 D |
| 4,235,412 | 11/1980 | Rath et al. | 251/10 |

Primary Examiner—Robert W. Michell
Assistant Examiner—Thomas Wallen
Attorney, Agent, or Firm—Paul C. Flattery; Q. Todd Dickinson; Daniel D. Ryan

[57] ABSTRACT

A separable integral donor connector with an improved clamping mechanism for use with flexible blood collection tubing is disclosed. The device is positioned in line with the blood tubing between a phlebotomy needle and the collection bag. Separation of the device is accomplished by manipulation and breaking of a thin frangible ring area and drawing the sections of the device apart. This separation exposes an internally-mounted needle that may be used for penetration of sample collection tube closures and subsequent collection of blood samples. The present embodiment of this invention includes improved manually-operated clamping jaws that are flexibly biased away from the blood tubing. Clamping jaws of differing lengths are disclosed which, when engaged, overlap and cause an area of tubing to be collapsed into a distinctive, S-shaped configuration which crimps and more effectively seals the tubing against blood flow. The clamping device is free from restraints permitting simple, one-handed operation, as well as the broadest control over the blood flow.

8 Claims, 7 Drawing Figures

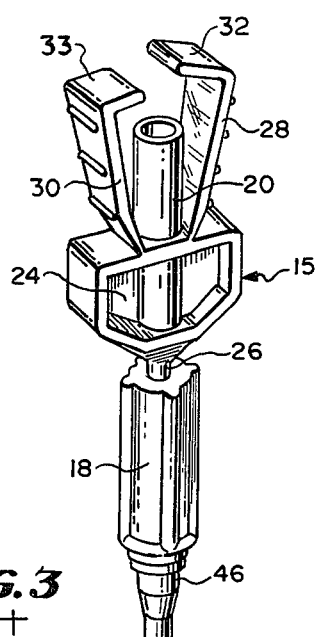
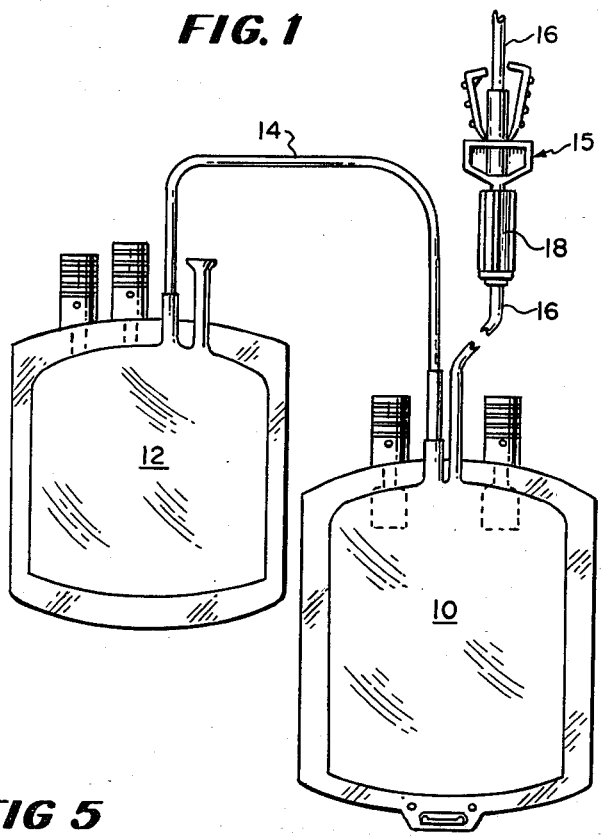
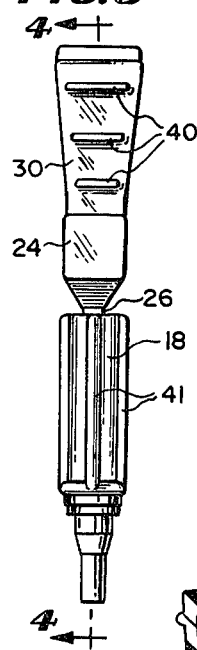
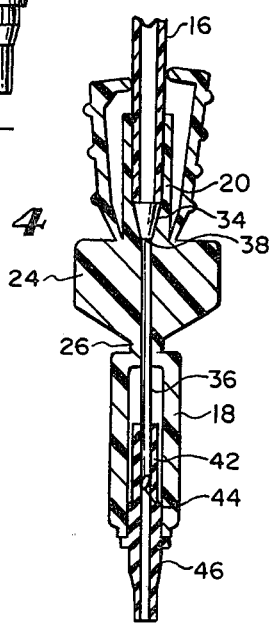
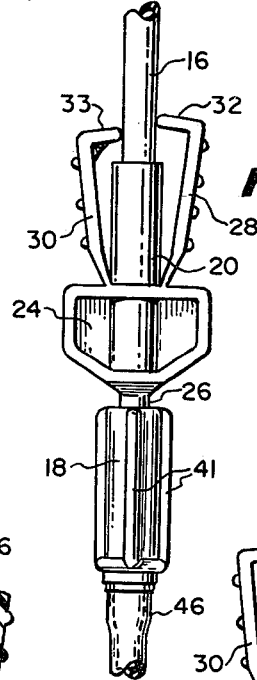
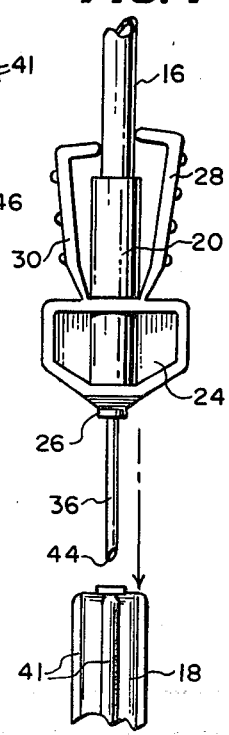
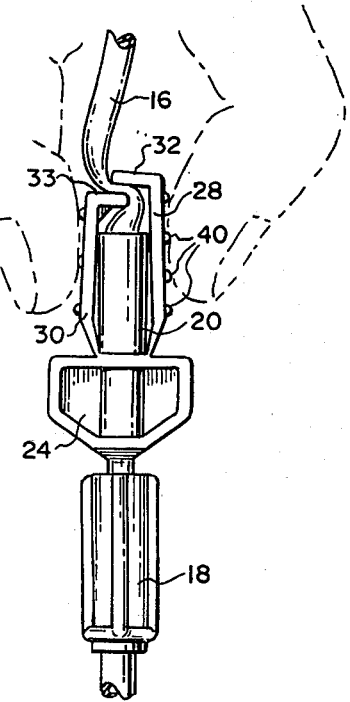

SEPARABLE INTEGRAL DONOR CONNECTOR WITH MANUAL CLAMPING MEANS

BACKGROUND OF THE INVENTION

The basic concept of one form of a separable integral donor connector has been previously described in U.S. Pat. No. 3,127,892 to Kuehn, issued Jan. 3, 1979 and assigned to the same assignee as the subject application. Separable integral donor (SID) connectors are used during blood collection to separate the donor tube from the blood collection bag and collect samples of the donor's blood without the necessity of removing the phlebotomy needle from the arm of the donor. After filling the blood collection bag, the separable integral donor connector is separated, exposing a hollow needle which is then inserted through the closure of a sample tube, permitting the collection of one or more samples of blood through the same donor tubing.

The present invention provides an improved version of a separable integral donor connector which has integral with it means for manually clamping the tubing so that the flow of the blood through the separable integral donor connector and into the sample tubes can be regulated and/or cut off when it is undesirable.

DESCRIPTION OF THE INVENTION

This application relates to a separable integral donor connector for use in collection tubing in a blood collection system, including a flexible plastic blood bag. The connector includes means for separating the device such that a hollow needle is exposed for the insertion of blood into sample collectors by puncturing of the closure of said sample collector tubes with the needle.

In accordance with this invention, the connector includes flexible blood tubing internally mounted within the device and positioned to permit flow through an internally-mounted needle. Also included in the device is a thin-walled frangible area which may be easily broken by manual manipulation, separating the tubing which leads to the blood bag from the donor tubing and exposing the needle for use.

Overlapping crimping jaws of differing lengths are provided. When engaged, the jaws do not oppose each other; rather, protruding arms on the ends of the jaws overlap and collapse the blood flow tubing twisting it and forcing it into an S-shaped configuration. This configuration results in the sealing of a broader area of flow tubing than would be accomplished if the crimping jaws met directly opposite each other, and a more effective regulation of blood flow.

The jaws are made of flexible, resilient material and are free from clamps or restraints. The jaws are biased away from the flow tubing so that when the jaws are manually released by the operator they disengage from the tubing and allow blood to flow through the flexible tubing. This feature permits the operator to have increased control and regulation over the blood flow during operation.

The device is also manufactured from flexible material to facilitate its breaking apart and separation, to expose the needle more smoothly, and to prevent the introduction of small pieces of plastic from the frangible area which are occasioned by the use of harder or more brittle plastics.

Referring to the drawings:

FIG. 1 is a plan view of a double blood bag collection system with blood donor tubing incorporating a preferred embodiment of the invention of this application.

FIG. 2 is a perspective view of the embodiment of the invention separate from the tubing.

FIG. 3 is a side view of the embodiment of the invention.

FIG. 4 is a cross-sectional view of the embodiment of the invention showing the internally-mounted needle.

FIG. 5 is a longitudinal view of the embodiment of the invention with the blood donor tubing incorporated.

FIG. 6 is a view similar to FIG. 5, but showing the embodiment of the invention with the crimping jaws activated, sealing the donor tubing.

FIG. 7 is a longitudinal view of the embodiment of the invention showing the device separated.

Referring to the drawings:

In FIG. 1 a multiple blood bag system is shown comprising flexible plastic blood bags 10, 12, connected by standard flexible blood transfer tubing 14. These are standard commercially available blood collection products such as those manufactured by the Fenwal Division of Baxter Travenol Laboratories, Deerfield, Ill. Donor tubing 16 connects blood collection bag 10 to a donor phlebotomy needle (not shown) and contains a separable integral donor connector 15 in line with the tubing 16.

As more specifically shown in FIGS. 2 through 5, the separable integral donor connector 15 contains two separable sections 18 and 24 connected by a thin, frangible flexible annular ring 26 which is manually manipulated and broken at the time of use. Second section 24 contains a set of crimping jaws 28, 30 one of which, 28, is longer than the other 30. The jaws 28, 30 are further defined by perpendicular protruding arms 32, 33. When engaged by manually compressing jaws 28, 30, arms 32, 33 overlap and collapse a section of tubing 16.

As shown in FIG. 6, by this collapsing, tubing 16 is twisted and crimped into an S-shaped configuration. This configuration more effectively blocks or controls the flow of blood through tubing 16 and hollow needle 36 by sealing a wider area of tubing 16 than would occur if the arms 32, 33 of jaws 28, 30 engaged directly opposite to each other.

Blood tubing 16 is integral with the separable integral donor connector 15 and internally secured at inlet port 20. The inlet port 20 is further defined by an internal bevelled area 34 which leads from tubing 16 to the inlet 38 of needle 36, providing a smooth and efficient blood flow path, and alleviating eddy currents in the blood flow at the juncture of the tubing 16 and the needle inlet 38. The prevention of eddy currents is important to avoid hemolysis caused by such currents at the juncture of the needle inlet 38 and the tubing 16.

Gripper ridges 40 are provided external to the crimping jaws 32, 33 to facilitate the grip of the operator on the separable integral donor connector 15 during manual operation. Ribs 41 are also provided on integral member 18 to facilitate the oppositely directed twisting of sections 18 and 24 and the breaking of frangible ring 26.

A protective sheath 42 surrounds and protects the tip 44 and bottom section of needle 36. The protective sheath 42 is constructed from material such that when the separable integral donor connector 15 is autoclaved for sterilization, the sheath 42 shrinks around and becomes integral with needle 36. This shrinking provides a unified blood flow path through the separable integral donor connector 15 and an uninterrupted sterile connection from donor to blood collection bag 10. The sheath 42 is internal of plastic member 18 and is integral with plug 46 which abuts and seals the lower end of member 18 and communicates member 18 with flexible tubing 16.

In operation, a unit of whole blood is collected from the donor in blood collection bag 10. After collection the tubing 16 between the separable integral donor connector 15 and blood bag 10 is heat-sealed, clipped, or sealed in some other conventional manner, to prevent blood loss from the blood collection bag 10 and preserve sterility, and the blood unit is removed for storage or processing.

Clamping jaws 28, 30 are manually compressed together in such a manner that extension arms 32 and 33 collapsibly crimp a section of flexible tubing 16, forcing tubing 16 into an S-shaped configuration, and cutting off the flow of blood.

As illustrated in FIG. 7, the two sections 18, 24 of the separable integral donor connector 15 are then manually manipulated such that frangible ring 26 is broken and needle 36 is drawn back from member 18 and exposed. Needle 36 may then be inserted in sample collection tubes (not shown) by puncturing a latex or rubber closure on such tubes.

To permit blood to flow for sample collection, clamping jaws 28, 30 are manually released allowing them to flexibly bias away from the blood tubing 16. The blood tubing 16 uncrimps, straightening from its S-shape, and blood flows through tubing 16 into a sample collection tube at a desired rate and until a desired quantity of blood is collected. Said clamping jaws 28, 30 are then re-engaged to cut off the blood flow and the needle 36 is withdrawn from the sample collection tube.

Jaws 28, 30 are free of any restraints or clamps of their own and can be used to regulate the rate of flow of blood through the tubing in addition to simply permitting or not permitting its flow. Reliability is promoted by the lack of restraint as well as ease of operation and control.

The needle 36 may be reinserted in other sample collection tubes, the jaws 28, 30 released, and another sample taken. After taking the desired number of samples, the tubing 16 is again crimped and the donor phlebotomy needle (not shown) is withdrawn from the arm of the donor. The separable integral donor connector 15 and the remaining tubing 16 may then be conveniently disposed of.

The above has been offered for illustrative purposes only and is not intended to limit the scope of the invention of this application, which is as defined in the claims below.

What is claimed is:

1. A device for controlling fluid flow through a flexible conduit, said device comprising
    a main body including means defining a fluid passage which extends axially therethrough and which is attachable in flow communication with the flexible conduit,
    first and second jaw members projecting outwardly beyond said main body on opposite sides and generally facing the axis of said fluid passage, each of said jaw members including, at its terminus, an arm portion extending radially inwardly toward the axis of said fluid passage, one of said arm portions being spaced a greater distance from said main body than the other one of said arm portions, and
    means operatively connecting said first and second jaw members to said main body for cooperative movement between a generally open position, in which said arm portions are disposed in a spaced apart relationship on opposite facing sides of the axis of said fluid passage to afford fluid flow through the flexible conduit attached thereto, and a generally closed position, in which said arm portions are disposed in a mutually overlapping position along the axis of said fluid passages to pinch between said overlapping arm portions a section of the flexible conduit and obstruct fluid flow therethrough.

2. A device for supporting a needle and for attaching the needle in flow communication with flexible conduit, said device comprising
    a main body including means defining a fluid passage which extends axially therethrough and which includes, at a first end thereof, means for attaching the needle in flow communication with said fluid passage and, at a second end thereof, means for attaching the flexible conduit in flow communication with said fluid passage and, thus, the needle,
    first and second jaw members projecting outwardly beyond said main body adjacent to said second fluid passage end on opposite sides of and generally facing the axis of said fluid passage, each of said jaw members including, at its terminus, an arm portion extending radially inwardly toward the axis of said fluid passage, one of said arm portions being spaced a greater distance from said main body than the other one of said arm portions, and
    means operatively connecting said first and second jaw members to said main body for cooperative movement between a generally open position, in which said arm portions are disposed in a spaced apart relationship on opposite facing sides of the axis of said fluid passage to afford fluid flow through the flexible conduit attached thereto, and a generally closed position, in which said arm portions are disposed in a mutually overlapping portion along the axis of said fluid passage to pinch between said overlapping arm portions a section of the flexible conduit and obstruct fluid flow therethrough.

3. A device according to claim 1 or 2
wherein said connection means of said first and second jaw members includes means for normally biasing said first and second jaw members toward said generally open position.

4. A device according to claim 3
wherein said first and second jaw members include spaced gripping ridges disposed along the exterior surfaces thereof.

5. A device according to claim 2
a further including an auxiliary body having an interior accommodating the needle when the needle is attached to said main body.

6. A device according to claim 5
wherein said auxiliary body includes, at one end thereof, means for attaching a fluid conduit in flow communication with said interior.

7. A device according to claim 5 or 6
and further including means for removably securing said auxiliary body to said main body with the needle attached to said main body disposed within said auxiliary body interior.

8. A device according to claim 7
wherein said securing means includes a frangible annular ring joining said member to said main body.

* * * * *